United States Patent [19]

Ohashi et al.

[11] Patent Number: 4,920,043
[45] Date of Patent: Apr. 24, 1990

[54] METHOD FOR PROCESSING SILVER HALIDE PHOTOGRAPHIC LIGHT-SENSITIVE MATERIAL

[75] Inventors: Minoru Ohashi; Shoichi Horii, both of Nagaokakyo, Japan

[73] Assignee: 501 Mitsubishi Paper Mills Limited, Tokyo, Japan

[21] Appl. No.: 323,873

[22] Filed: Mar. 15, 1989

[30] Foreign Application Priority Data

Mar. 18, 1988 [JP] Japan .................................. 63-66186
Mar. 22, 1988 [JP] Japan .................................. 63-68452
Oct. 12, 1988 [JP] Japan ................................. 63-257638

[51] Int. Cl.$^5$ ............................................. G03C 1/34
[52] U.S. Cl. .................................... 430/611; 430/445; 430/446; 430/489; 430/614
[58] Field of Search ............... 430/489, 611, 445, 446, 430/614

[56] References Cited

U.S. PATENT DOCUMENTS

4,610,954  9/1986  Torigoe et al. ....................... 430/445
4,657,847  4/1987  Ikeda et al. .......................... 430/611
4,720,451  1/1988  Shuto et al. .......................... 430/611

Primary Examiner—Paul R. Michl
Assistant Examiner—Thorl Chea
Attorney, Agent, or Firm—Cushman, Darby & Cushman

[57] ABSTRACT

The present invention provides a method for photographic processing of a silver halide photographic light-sensitive material with high sensitivity and with less fog. This method comprises imagewise exposing a silver halide photographic light-sensitive material and then developing the exposed light-sensitive material in the presence of at least one compound selected from the group consisting of the compounds represented by the following formulas (I)–(IV):

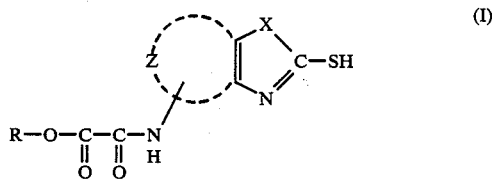

(I)

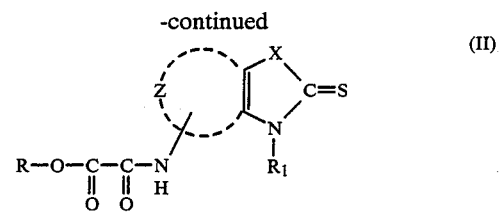

(II)

wherein Z represents a group of atoms necessary to form a condensed aromatic ring which may have a substituent in addition to

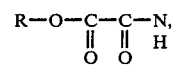

R represents a hydrogen atom or a monovalent organic group, $R_1$ represents a hydrogen atom or a substituted or unsubstituted alkyl group and X represents an oxygen atom, a sulfur atom, a selenium atom or $>N-R_2$ wherein $R_2$ represents a hydrogen atom or a substituted or unsubstituted alkyl group;

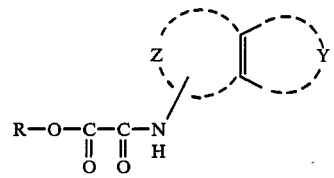

wherein Y represents a group of atoms necessary to form a heterocyclic ring having two or more nitrogen atoms, Z represents a group of atoms necessary to form a condensed aromatic ring which may have a substituent in addition to

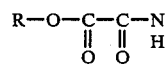

and R represents a hydrogen atom or a monovalent organic group; and

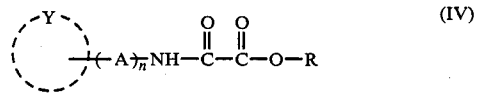
(IV)

wherein Y represents a group of atoms necessary to form a nitrogen-containing heterocyclic ring containing no condensed aromatic ring, R represents a hydrogen atom or a monovalent organic group, A represents an arylene group and n is 0 or 1.

9 Claims, No Drawings

METHOD FOR PROCESSING SILVER HALIDE PHOTOGRAPHIC LIGHT-SENSITIVE MATERIAL

BACKGROUND OF THE INVENTION

The present invention relates to a method for processing a silver halide photographic light-sensitive material which uses an antifoggant.

It is well known that silver halide photographic light-sensitive materials change with time in photographic characteristics such as sensitivity, fog and color tone during storage. Further, owing to recent demand for shortening of access time, so-called high-temperature high-speed processing which employs higher processing temperature and shorter processing time than conventional method has been often carried out and thus the materials are under the condition at which especially fogging occurs easily.

Up to now there have been found a lot of stabilizers and antifoggants for preventing and decreasing increase of fog during storage and occurrence of fog during development and were applied for patents. However, the compounds which exhibit higher fog preventive effect tend to reduce sensitivity of light-sensitive material and those compounds which satisfy both the retention of sensitivity and the prevention of fogging have not yet been found.

Japanese Patent Kokai Nos. 36130/76, 121,432/80 and 126,234/80 disclose techniques to sensitize with known antifoggants, but these techniques still suffer from the defects that it depends on crystal habit of silver halide or kind of sensitizing dye and that fog increases or contrast decreases.

SUMMARY OF THE INVENTION

An object of the present invention is to provide a method for processing silver halide photographic light-sensitive materials with high sensitivity and little fog.

Another object of the present invention is to provide a silver halide photographic light-sensitive material prevented from fogging and increased in sensitivity.

The inventors have found that antifoggants having a specific substituent can attain the above objects.

DESCRIPTION OF THE INVENTION

That is, the present invention is a photographic processing method which is characterized by developing a silver halide photographic light-sensitive material in the presence of at least one compound selected from the compounds represented by the following formulas (I), (II), (III) and (IV):

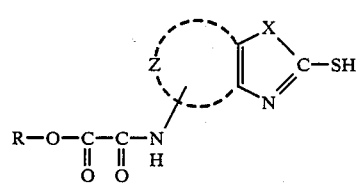

(I)

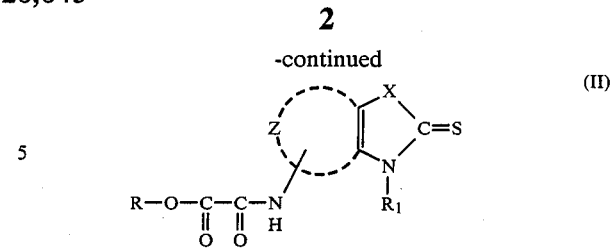

wherein Z represents a group of atoms necessary to form a condensed aromatic ring such as benzene ring, naphthalene ring or the like which may have substituent other than —NHCOCOOR; the substituents which the condensed aromatic ring may have include halogen atoms (such as F, Cl, Br and the like), substituted or unsubstituted alkyl groups (such as methyl, trifluoromethyl, ethyl, n-octyl, and benzyl), substituted or unsubstituted aryl groups (such as phenyl and p-chlorophenyl), substituted or unsubstituted alkoxy groups and aryloxy groups (such as methoxy, n-hexyloxy, phenoxy and n-octyloxy), sulfonyl groups (such as methanesulfonyl and p-toluenesulfonyl), sulfonamide groups (such as n-octanesulfonamide and p-toluenesulfonamide), sulfonamide), sulfamoyl groups (such as diethylsulfamoyl and 4-chlorophenylsulfamoyl), carbamoyl groups (such as n-butylcarbamoyl and 4-cyanophenylcarbamoyl), amide groups (such as n-hexaneamide, n-decaneamide and benzamide), ureido groups (such as 3-butylureido and morpholinocarbonylamino), aryl or alkoxycarbonylamino groups (such as ethoxycarbonylamino, iso-butylcarbonylamino and phenoxycarbonylamino), aryl or alkoxycarbonyl groups (such as ethoxycarbonyl or phenoxycarbonyl), aryl or alkylaminocarbonyloxy groups (such as phenylaminocarbonyloxy and iso-butylaminocarbonyloxy), cyano group, alkyl or arylthio groups (such as n-octylthio and 2-methoxycarbonylphenylthio); X represents an oxygen atom, a sulfur atom, a selenium atom or $>$N—$R_2$ (wherein $R_2$ represents a hydrogen atom or substituted or unsubstituted alkyl group); and $R_1$ represents a hydrogen atom or a substituted or unsubstituted alkyl group. The antifoggant of the present invention is characterized by having at least one substituent represented by the formula:

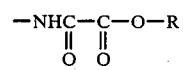

in condensed aromatic ring. In this formula, R represents a hydrogen atom or a monovalent organic group such as an alkyl group, an aryl group, an alkenyl group, a heterocyclic group, a substituted amino group or the like. The alkyl group and alkenyl group of R are preferably alkyl group and alkenyl group having 20 or less carbon atoms which may have substituents such as halogen atom, cyano group, carboxyl group, alkoxy group (including polyether group), aryloxy group, sulfo group, aryl group and substituted amino group. The aryl group of R includes phenyl and naphthyl groups and may have substituents such as alkyl group, aryl group, halogen atom, alkoxy group, aryloxy group, alkenyl group, substituted amino group, acylamino group, sulfonamide group, alkylideneamino group and heterocyclic group. The heterocyclic group of R includes, for example, pyridyl group, pyrazinyl group, pyridazinyl group, quinolyl group, isoquinolyl group, phthalazinyl group, naphthyridinyl group, quinoxalinyl group, quinazolinyl group, cinnolinyl group and pteridinyl group and these heterocyclic groups may have substituents such as alkyl group, aryl group, halogen atom, substituted amino group, cyano group, acylamino group, carboxyl group, alkoxycarbonyl group and aryloxycarbonyl group. The substituted amino group of R includes amino groups substituted with alkyl group, aryl group, heterocyclic group or the like and heterocyclic ring formed together with nitrogen atom of the amino group;

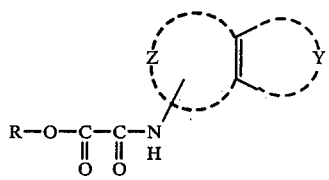
(III)

where Y represents a group of atoms which form a heterocyclic ring having at least two nitrogen atoms, Z represents a group of atoms which form a condensed aromatic ring which may have a substituent in addition to the substituent shown in the formula and R represents a hydrogen atom or a monovalent organic group. In the above formula (III), Z represents a group of atoms necessary to form a condensed aromatic ring such as, for example, benzene ring and naphthalene ring which may have a substituent in addition to —NHCOCOOR. The additional substituent of the condensed aromatic ring includes, for example, halogen atoms (such as F, Cl, and Br), substituted or unsubstituted alkyl groups (such as methyl, trifluoromethyl, ethyl, n-octyl and benzyl), substituted or unsubstituted aryl groups (such as phenyl and p-chlorophenyl), substituted or unsubstituted alkoxy and aryloxy groups (such as methoxy, n-hexyloxy, phenoxy and n-octyl), sulfonyl groups (such as methanesulfonyl and p-toluenesulfonyl), sulfonamide groups (such as n-octanesulfonamide and p-toluenesulfonamide), sulfamoyl groups (such as diethylsulfamoyl and 4-chlorophenylsulfamoyl), carbamoyl groups (such as n-butylcarbamoyl and 4-cyanophenylcarbamoyl), amide groups (n-hexaneamide, n-decaneamide and benzamide), ureido groups (such as 3-butylureido and morpholino-carbonylamino), aryl or alkoxycarbonylamino groups (such as ethoxycarbonylamino, iso-butylcarbonylamino and phenoxycarbonylamino), aryl or alkoxycarbonyl groups (such as ethoxycarbonyl and phenoxycarbonyl), aryl or alkylaminocarbonyloxy groups (such as phenylaminocarbonyloxy and iso-butylaminocarbonyloxy), cyano group, alkyl or arylthio groups (such as n-octylthio and 2-methoxycarbonylphenylthio). The condensed aromatic ring may contain two or more —NHCOCOOR. The heteroring formed by Y is preferably 5-membered or 6-membered rings having 2-3 nitrogen atoms such as diazole ring, trizaole ring, pyrazine ring and pyridazine ring. These heterorings may be substituted with alkyl groups (lower alkyl groups such as methyl, ethyl and propyl and alkyl groups substituted with hydroxyl or carboxyl group), hydroxyl group, carboxyl group and amino group.

R of

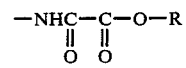

is the same as defined in the formulas (I) and (II).

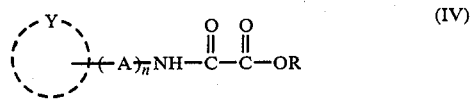
(IV)

wherein Y represents a group of atoms necessary to form a nitrogen-containing heterocyclic ring containing no condensed aromatic ring, R represents a hydrogen atom or a monovalent organic group, A represents an arylene group and n is 0 or 1. The nitrogen-containing heterocyclic compound represented by the above formula (IV) is a 5- or 6-membered nitrogen-containing heterocyclic ring where aromatic rings such as benzene ring and naphthalene ring are not condensed. As example thereof, mention may be made of imidazoline, imidazole, imidazolone, pyrazole, oxazoline, oxazole, oxazolone, thiazoline, thiazole, thiazolone, selenazoline, selenazole, selenazolone, oxadiazole, thiadiazole, triazole, tetrazole, pyrazine, pyrimidine, pyridazine, triazine, oxazine, thiazine, tetrazine and polyazaindene.

These nitrogen-containing heterocyclic rings may have optional substituents. Examples of the substituents are mercapto group, halogen atoms (such as F, Cl, Br and the like), substituted or unsubstituted alkyl groups (such as methyl, trifluoromethyl, ethyl, n-octyl, and benzyl), substituted or unsubstituted aryl groups (such as phenyl and p-chlorophenyl), substituted or unsubstituted alkoxy groups and aryloxy groups (such as methoxy, n-hexyloxy, phenoxy and n-octyloxy), hydroxyl group, sulfonyl groups (such as methanesulfonyl and p-toluenesulfonyl), sulfonamide groups (such as n-octanesulfonamide and p-toluenesulfonamide), sulfamoyl groups (such as diethylsulfamoyl and 4-chlorophenylsulfamoyl), acylamide groups (such as acetylamide), carbamoyl groups (such as n-butylcarbamoyl and 4-cyanophenylcarbamoyl), amino group, amide groups (such as n-hexaneamide, n-decaneamide and benzamide), ureido groups (such as 3-butylureido and morpholinocarbonylamino), aryl or alkoxycarbonylamino groups (such as ethoxycarbonylamino, iso-butylcarbonylamino and phenoxycarbonylamino), aryl or alkoxycarbonyl groups (such as ethoxycarbonyl and phenoxycarbonyl), aryl or alkylaminocarbonyloxy groups (such as phenylaminocarbonyloxy and iso-butylaminocarbonyloxy), cyano group, nitro group, alkenyl groups (such as allyl), and alkyl or arylthio groups (such as n-octylthio and 2-methoxycarbonylphenylthio).

The substituent —NHCOCOOR may directly bonds to said nitrogen-containing heterocyclic ring or may be substituted in the substituents mentioned above. The nitrogen-containing heterocyclic ring may have two or more —NHCOCOOR groups. R in this substituent has the same meanings as defined in Formulas (I)–(III).

Representative examples of the antifoggants of the formulas (I) and (II) are shown below.

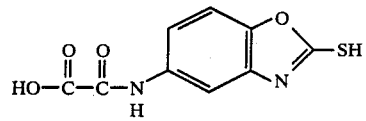 (I)-(1)
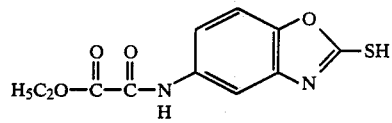 (I)-(2)
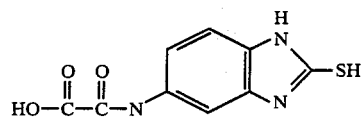 (I)-(3)
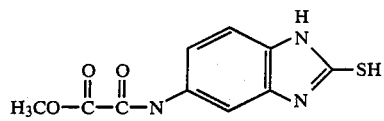 (I)-(4)
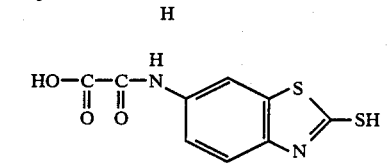 (I)-(5)
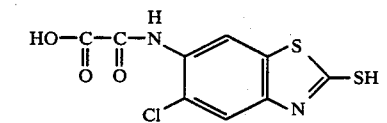 (I)-(6)
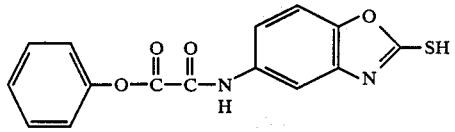 (I)-(7)
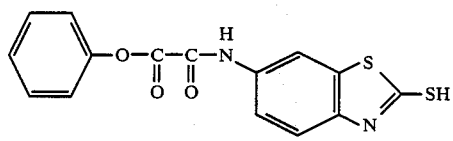 (I)-(8)
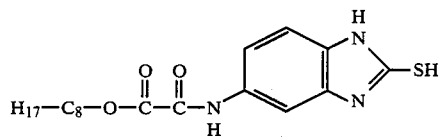 (II)-(9)
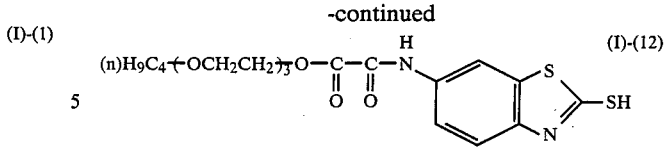 (I)-(10)
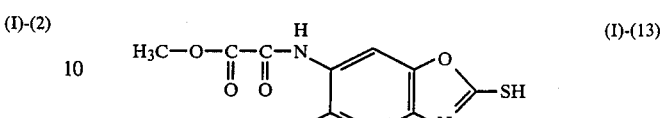 (I)-(11)
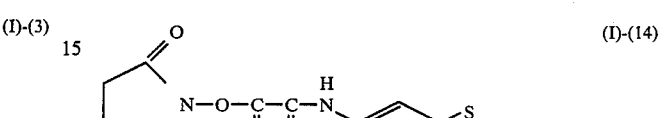 (I)-(12)
 (I)-(13)
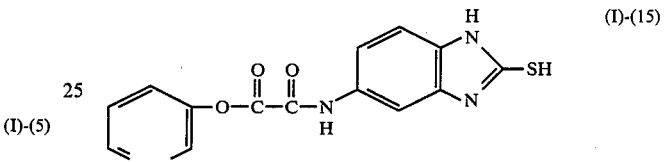 (I)-(14)
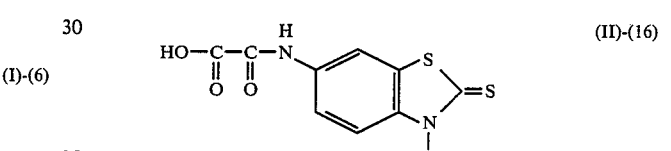 (I)-(15)
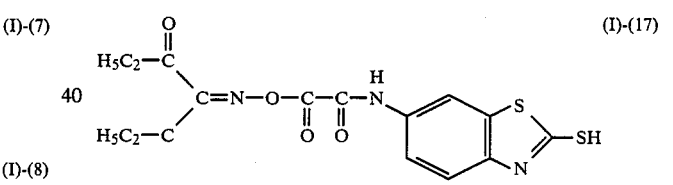 (II)-(16)
 (I)-(17)
Representative examples of the antifiggants of the formula (III) are shown below.
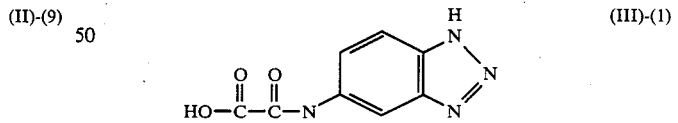 (III)-(1)
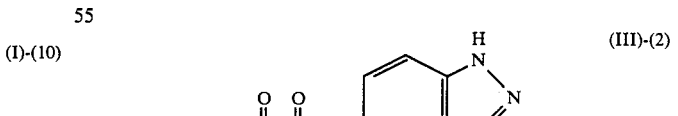 (III)-(2)
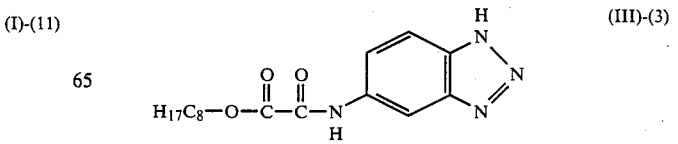 (III)-(3)

-continued
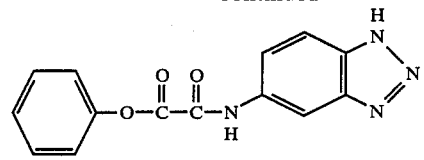 (III)-(4)
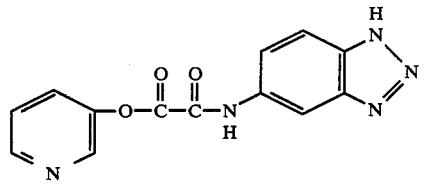 (III)-(5)
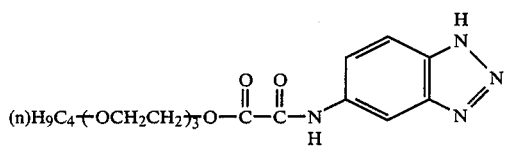 (III)-(6)
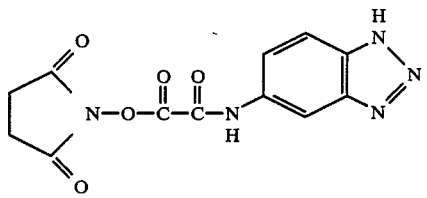 (III)-(7)
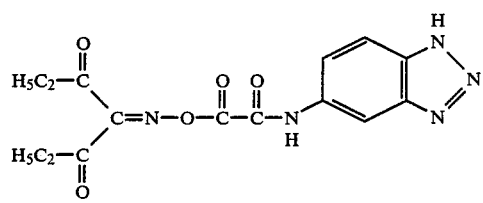 (III)-(8)
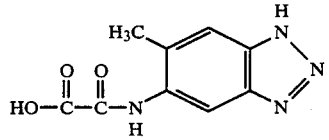 (III)-(9)
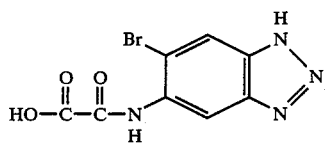 (III)-(10)
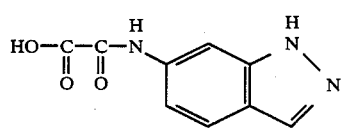 (III)-(11)
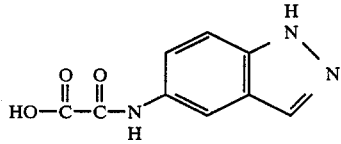 (III)-(12)
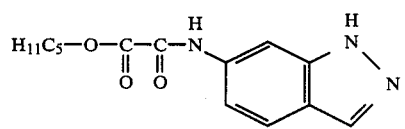 (III)-(13)
-continued
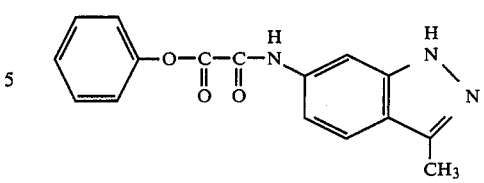 (III)-(14)
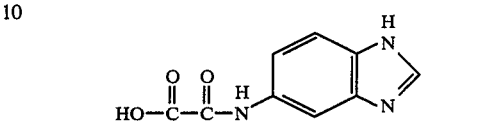 (III)-(15)
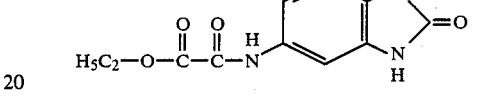 (III)-(16)
Representative examples of the antifiggants of the formula (IV) are shown below.
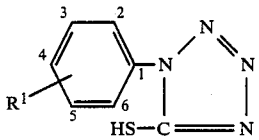
| Compound No. | R¹ | Position of R¹ |
|---|---|---|
| (IV)-(1) | 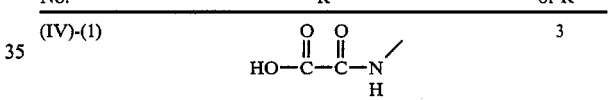 | 3 |
| (IV)-(2) | 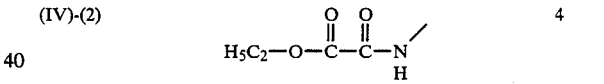 | 4 |
| (IV)-(3) | 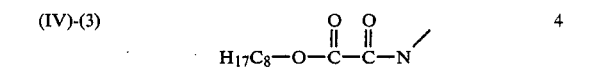 | 4 |
| (IV)-(4) | 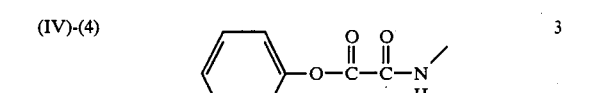 | 3 |
| (IV)-(5) | 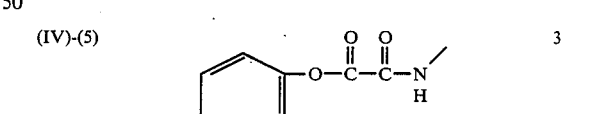 | 3 |
| (IV)-(6) |  | 4 |
| (IV)-(7) | 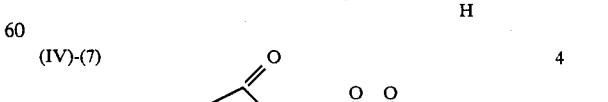 | 4 |

-continued

[Structure: phenyl ring with positions 2,3,4,5,6 labeled, N1 attached to tetrazole ring with HS–C=N]

| Compound No. | R¹ | Position of R¹ |
|---|---|---|
| (IV)-(8) | $H_5C_2-CO-C(=N-O-CO-CO-NH-CH_3)-CO-C_2H_5$ | 3 |

[Structure: thiadiazole ring with R² and R³ substituents]

| | R² | R³ |
|---|---|---|
| (IV)-(9) | H | $HO-CO-CO-NH-CH_3$ |
| (IV)-(10) | —SH | $HO-CO-CO-NH-CH_3$ |
| (IV)-(11) | —SH | $H_{11}C_5-O-CO-CO-NH-CH_3$ |
| (IV)-(12) | —SH | $C_6H_5-O-CO-CO-NH-CH_3$ |
| (IV)-(13) | —SH | 3-pyridyl-$O-CO-CO-NH_2$ |
| (IV)-(14) | —SH | $HO-CO-CO-NH-C_6H_4-CH_3$ (p-tolyl) |

[Structure: oxadiazole ring with R⁴ and R⁵ substituents]

| | R⁴ | R⁵ |
|---|---|---|
| (IV)-(15) | —SH | $HO-CO-CO-NH_2$ |
| (IV)-(16) | —SH | $H_3C-O-CO-CO-NH-CH_3$ |
| (IV)-(17) | —SH | succinimido-$O-CO-CO-NH-CH_3$ |
| (IV)-(18) | —SH | $H_{17}C_8-O-CO-CO-NH-CH_3$ |

[Structure: triazole ring with HS, R⁶ (on N), and R⁷ substituents]

| | R⁶ | R⁷ |
|---|---|---|
| (IV)-(19) | $HO-CO-CO-NH-CH_3$ | H |
| (IV)-(20) | H | $HO-CO-CO-NH-CH_3$ |
| (IV)-(21) | $H_9C_4O-CO-CO-NH-$ | $H_9C_4-$ |
| (IV)-(22) | $C_6H_5-O-CO-CO-NH-$ | $H_2N-$ |
| (IV)-(23) | $H_2N-$ | $HO-CO-CO-NH-CH_3$ |
| (IV)-(24) | $(n)H_{21}C_{10}O-CO-CO-NH-$ | H |
| (IV)-(25) | 2,4-di-t-butylphenyl-$O-CO-CO-NH-$ | H |
| (IV)-(26) | $C_6H_5-O-CO-CO-NH-$ | $C_6H_5-$ |

PREPARATION EXAMPLE 1

[Preparation of Compound (I)–(10)]

36.4 g of 6-amino-2-mercaptobenzothiazole and 40.6 g of phenyloxalyl chloride were suspended in 500 ml of benzene with stirring, during which 30.7 ml of triethylamine was added gradually and dropwise thereto, followed by stirring at room temperature for about 1 hour and then refluxing with heating for about 1.5 hour.

After the reaction, the reaction mixture was put in water and extracted with ethyl acetate. The resulting organic layer was washed with water and dried over anhydrous sodium sulfate. After drying, the solvent was distilled off under reduced pressure and the resulting crude crystal was recrystallized from dioxane to obtain the objective compound.

Yield: 36.5 g.

Melting point: 300° C. or higher.

|  | Elemental analysis | | |
| --- | --- | --- | --- |
|  | C (%) | H (%) | N (%) |
| Calcd. | 54.53 | 3.05 | 8.48 |
| Found | 54.33 | 3.08 | 8.76 |

PREPARATION EXAMPLE 2

[Preparation of Compound (I)–(5)]

6.6 g of compound (I)–(5) obtained in Preparation Example 1 was added to 60 ml of 1N aqueous potassium hydroxide solution. After 3 hours, the solution was stirred at room temperature and then 1N hydrochloric acid was added thereto to make acidic the pH of the reaction mixture. The precipitated crystal was collected by filtration, washed with water and then dried to obtain the objective compound (I)–(5).

Yield: 4.2 g.

Melting point: 300° C. or higher.

|  | Elemental analysis | | |
| --- | --- | --- | --- |
|  | C (%) | H (%) | N (%) |
| Calcd. | 42.51 | 2.38 | 11.02 |
| Found | 42.30 | 2.51 | 11.00 |

PREPARATION EXAMPLE 3

[Preparation of Compound (III)–(4)]

13.4 g of 5-aminobenzotriazole was dissolved in 100 ml of dioxane. Then, 7.9 g of pyridine was added to the solution and thereto was further added dropwise a solution of 18.5 g of phenoxalyl chloride in 80 ml of dioxane at room temperature with stirring. After stirring for about 4 hours at the above temperature, the precipitated crystal was collected by filtration and this crude crystal was washed with water and recrystallized from ethanol to obtain the objective compound (III)–(4).

Yield: 19.5 g.

Melting point: 300° C. or higher.

|  | Elemental analysis | | |
| --- | --- | --- | --- |
|  | C (%) | H (%) | N (%) |
| Calcd. | 59.57 | 3.57 | 17.01 |
| Found | 58.96 | 3.63 | 17.03 |

PREPARATION EXAMPLE 4

[Preparation of Compound (III)–(1)]

To 1.7 g of compound (III)–(4) obtained in Preparation Example 3 was added 20 ml of 1N aqueous NaOH solution, followed by stirring at room temperature for about 3 hours. After termination of the reaction, 1N aqueous HCl solution was added to neutralize the reaction mixture and the precipitated crystal was collected by filtration, washed with water and then dried to obtain the objective compound (III)–(1).

Yield: 0.96 g.

Melting point: 264°–265° C. (decomposition).

|  | Elemental analysis | | |
| --- | --- | --- | --- |
|  | C (%) | H (%) | N (%) |
| Calcd. | 46.60 | 2.93 | 23.28 |
| Found | 46.50 | 2.98 | 23.25 |

PREPARATION EXAMPLE 5

[Preparation of Compound (IV)–(4)]

300 ml of benzene was added to 9.65 g of 1-(m-aminophenyl)-5-mercaptotetrazole and 9.3 g of phenoxalyl chloride and thereto was added dropwise 6.98 ml of triethylamine at room temperature with stirring. After completion of the addition, the mixture was stirred at this temperature for 2 hours and then refluxed with heating for 2 hours. After the reaction, the solvent was distilled off under reduced pressure and water was added to the residue and this was left to stand for a while to precipitate crystal. This crude crystal was collected by filtration and recrystallized from ethyl acetate-ligroine to obtain the objective compound.

Yield: 3.34 g.

Melting point: 175.0°–175.5° C.

|  | Elemental analysis | | |
| --- | --- | --- | --- |
|  | C (%) | H (%) | N (%) |
| Calcd. | 52.78 | 3.25 | 20.52 |
| Found | 52.98 | 3.22 | 20.48 |

PREPARATION EXAMPLE 6

[Preparation of Compound (IV)–(1)]

To 1.03 g of compound (IV)–(4) prepared in Preparation Example 5 was added 9 ml of 1N aqueous KOH solution, followed by stirring at room temperature for 2.5 hour. To the reaction mixture was added 9 ml of 1N aqueous HCl solution and the precipitated crystal was collected by filtration, washed with water and then methanol and dried to obtain compound (IV)–(1).

Yield: 0.46 g.

Melting point: 189° C. (decomposition).

|  | Elemental analysis | | |
| --- | --- | --- | --- |
|  | C (%) | H (%) | N (%) |
| Calcd. | 40.75 | 2.66 | 26.41 |
| Found | 40.85 | 2.60 | 26.83 |

According to the method of the present invention, exposed silver halide photographic light-sensitive material is developed with various developers in the presence of the antifoggant of the present invention.

The antifoggant can be allowed to exist at the time of development by various means, but preferably it is added to a silver halide emulsion layer of a photographic light-sensitive material or to a water permeable colloid layer contiguous to the emulsion layer, for example, overcoat layer or undercoat layer for the emulsion layer or to a developer or a pre-bath of the developer.

The antifoggant of the present invention has markedly excellent effects to effectively prevent fogging and besides, to increase sensitivity of silver halide photographic light-sensitive material. This effect is exhibited not only at ordinary exposure, but also at high-intensity short-time exposure.

The antifoggant of the present invention is dissolved in water or in a water-miscible solvent such as D.M.F., methanol, ethanol, or an aqueous alkali solution and the solution is added to the above silver halide emulsion or the above colloid dispersion and mixed before coating on a support. Thus, the antifoggant can be added to the silver halide emulsion or the colloid dispersion.

Furthermore, it is also possible to disperse the antifoggant in latex and to add the dispersion to the silver halide emulsion or the colloid dispersion as shown in Japanese Patent Kokai No. 137,131/78.

When it is added to a processing solution, it can be added as it is or can be dissolved in a water-miscible solvent such as D.M.F., methanol or ethanol and added as a solution.

When the antifoggant is added to silver halide photographic light-sensitive material, amount of the antifoggant is normally $10^{-6}-10^{-2}$ mol, preferably $10^{-5}-10^{-2}$ mol per 1 mol of silver halide and when it is added to a processing solution, its amount is normally $10^{-5}-10^{-1}$ mol/1, preferably $10^{-4}-10^{-2}$ mol/1.

The present invention can use known processing solutions and known processing methods except for addition of the antifoggant of the present invention, and can be applied to both the development treatment which forms silver image (including monochromatic photographic treatment and diffusion transfer treatment) and the development treatment which forms dye image (color photographic treatment).

Developer used for monochromatic photographic treatment can contain known developing agent. As the developing agent, mention may be made of, for example, dihydroxybenzenes (such as hydroquinone), 3-pyrazolidones (such as 1-phenyl-3-pyrazolidone), aminophenols (such as N-methyl-p-aminophenol), hydroxylamines (such as N,N-diethylhydroxylamine), ascorbic acid and heterocyclic compounds such as those prepared by condensation of 1,2,3,4-tetrahydroquinoline ring and indolene ring as disclosed in U.S. Pat. No. 4,067,872. These may be used alone or in combination.

The developer used for color photographic treatment can contain known developing agent. As the developing agent, mention may be made of, for example, phenylenediamines such as 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 5-methyl-4-amino-N-ethyl-N-β-methanesulfoamidoethylaniline and 4-amino-3-methyl-N-ethyl-N-β-methoxyethylaniline and aminophenols. These may be used alone or in combination.

Generally, the developer further contains known preservative, alkali agent, pH buffer, antifoggant other than the antifoggant of the present invention and the like and, if necessary, may further contain silver halide solvent, toning agent, development accelerator, surface active agent, defoamer, water softener, hardener, viscosity imparting agent and the like.

As fixing solution, there may be used those of the generally used composition. As fixing agent, there may be used organic sulfur compounds known to have the effect of fixing agent in addition to thiosulfates and thiocyanates. The fixing solution may contain a water-soluble aluminum salt as a hardener.

The method of the present invention can be applied to various known silver halide photographic light-sensitive materials.

Silver halide emulsions which can be used in the present invention includes, for example, spectrally sensitized emulsions and non-sensitized emulsions, X-ray emulsions, and infrared sensitive emulsions and these may be either high speed negative emulsions or low speed positive emulsions and moreover may be either orthochromatic or panchromatic type.

Various silver salts can be used as light-sensitive silver salts. Examples thereof are silver bromide, silver iodide, silver chloride and mixed silver halides (such as silver chlorobromide and silver iodobromide).

Silver halides can be dispersed in ordinary hydrophilic colloids such as gelatin, casein, polyvinyl alcohol and carboxymethylcellulose. Among them, gelatin is preferred.

Silver halide emulsion is chemically sensitizable and can be chemically sensitized by ripening it in the presence of a small amount of sulfur-containing compounds (such as aryl thiocyanate, allylthiourea and sodium thiosulfate).

The emulsion can also be sensitized with reducing agents (such as tin compounds disclosed in French Patent No. 1,146,955 and U.S. Pat. No. 2,487,850 and imino-aminomethanesulfinic acid as disclosed in British Pat. No. 789,823) and a small amount of noble metals (such as gold, platinum, palladium, iridium, ruthenium and rhodium).

Silver halide emulsion layer and other waterpermeable colloid layers can also contain other additives such as development accelerator, sensitizer, antioxidant, hardener, surface active agent, brightening agent, color image forming coupler, and DIR coupler which are known in the photographic field.

Furthermore, the antifoggant of the present invention can be used in combination with other antifoggants or antifoggant precursors.

The present invention is further explained by the following examples.

EXAMPLE 1

Normally used surface active agent and hardener were added to an emulsion for chlorobromide photographic paper which comprised silver halide composed of 1 mol % of silver iodide, 47 mol % of silver bromide and 52 mol % of silver chloride and this emulsion was divided into six parts.

One of them was used as a control sample and to each of other parts was added a solution of the compound of the present invention or the following comparative compound in methanol in an amount of $1.5 \times 10^{-3}$ mol per 1 of silver halide. All of these emulsions were coated on a polyethylene-coated paper support at a coverage of 1.5 g/m² in terms of silver.

These samples were exposed through an optical wedge and developed with D-72 developer at 20° C. for 90 seconds. These samples were subjected to sensitometry. Separately, samples which had not been exposed were developed with D-72 developer at 30° C. for 5 minutes and fog density was measured to obtain the following results.

The following three compounds were used as comparative compounds.

Comparative Compound A

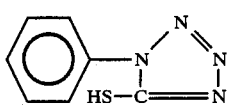

Comparative Compound B

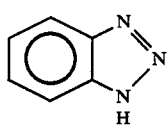

Comparative Compound C

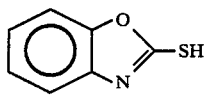

| Samples | Antifoggant | Relative density | Fog |
|---|---|---|---|
| 1 (control) | No | 100 | 0.22 |
| 2 | Compound (I)-(1) | 121 | 0.08 |
| 3 | Compound (I)-(3) | 126 | 0.08 |
| 4 | Comparative Compound A | 93 | 0.07 |
| 5 | Comparative Compound B | 99 | 0.18 |
| 6 | Comparative Compound C | 96 | 0.13 |

EXAMPLE 2

Sample 1 of Example 1 (photographic paper containing no antifoggant) was developed with D-72 developer containing $7.5 \times 10^{-4}$ mol/l of antifoggant in the same manner as in Example 1 to obtain the following results.

| Developer | Antifoggant | Relative sensitivity | Fog |
|---|---|---|---|
| 1 (control) | No | 100 | 0.22 |
| 2 | Compound (I)-(1) | 96 | 0.06 |
| 3 | Compound (I)-(5) | 97 | 0.06 |
| 4 | Compound (I)-(7) | 96 | 0.07 |
| 5 | Compound (I)-(15) | 97 | 0.07 |
| 6 | Compound (II)-(16) | 97 | 0.06 |
| 7 | Comparative Compound C | 91 | 0.09 |
| 8 | Comparative Compound D | 93 | 0.12 |

| Developer | Antifoggant | Relative sensitivity | Fog |
|---|---|---|---|

Comparative Compound (D)

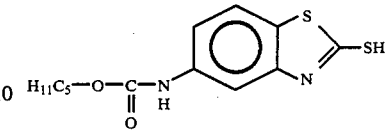

EXAMPLE 3

A cubic silver chloride of 0.34 μm in average grain size was chemically sensitized, followed by adding the following sensitizing dye in an amount of $5 \times 10^{-5}$ mol per 1 mol of silver halide and further adding a surface active agent and 2,4-dichloro-6-hydroxy-1,3,5-triazine (Na salt). This emulsion was coated on a polyester film support at a coverage of 5 g/m² in terms of silver.

Sensitizing dye

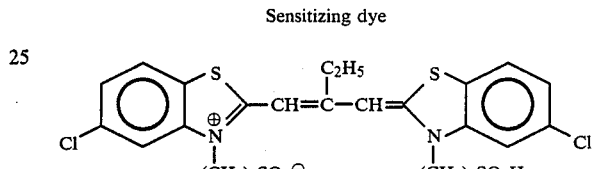

The sample was exposed through an optical wedge for $10^{-5}$ second and developed with PQ developer at 30° C. for 60 seconds and was subjected to sensitometry. Amount of antifoggant added to the emulsion was $2 \times 10^{-3}$ mol per 1 mol of silver halide. The following results were obtained.

| Sample | Antifoggant | Relative density | Fog |
|---|---|---|---|
| 1 (control) | No | 100 | 0.09 |
| 2 | Compound (I)-(5) | 134 | 0.02 |
| 3 | Compound (I)-(14) | 121 | 0.02 |
| 4 | Comparative Compound D | 97 | 0.05 |

EXAMPLE 4

Normally used surface active agent and hardener were added to an emulsion for chlorobromide photographic paper which comprised silver halide composed of 1 mol % of silver iodide, 47 mol % of silver bromide and 52 mol % of silver chloride and this emulsion was divided into six parts.

One of them was used as a control sample and to each of other parts was added $4 \times 10^{-3}$ mol (per 1 mol of silver halide) of the compound of the present invention or the following comparative compound dissolved in methanol. All of these emulsions were coated on a polyethylene-coated paper support at a coverage of 1.5 g/m² in terms of silver.

These samples were exposed through an optical wedge and developed with D-72 developer at 20° C. for 90 seconds. These samples were subjected to sensitometry. Separately, samples which had not been exposed were developed with D-72 developer at 30° C. for 5 minutes and fog density was measured to obtain the following results.

The following three compounds were used as comparative compounds.

Comparative Compound A

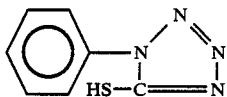

Comparative Compound B

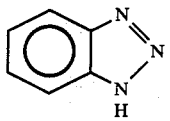

Comparative Compound C

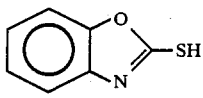

| Samples | Antifoggant | Relative density | Fog |
|---|---|---|---|
| 1 (control) | No | 100 | 0.22 |
| 2 | Compound (III)-(1) | 106 | 0.07 |
| 3 | Compound (III)-(12) | 105 | 0.06 |
| 4 | Comparative Compound A | 82 | 0.05 |
| 5 | Comparative Compound B | 90 | 0.14 |
| 6 | Comparative Compound C | 87 | 0.10 |

EXAMPLE 5

Sample 1 of Example 4 (photographic paper containing no antifoggant) was developed with D-72 developer containing $2\times10^{-3}$ mol/l of antifoggant in the same manner as in Example 4 to obtain the following results.

| Developer | Antifoggant | Relative sensitivity | Fog |
|---|---|---|---|
| 1 (control) | No | 100 | 0.22 |
| 2 | Compound (III)-(4) | 98 | 0.12 |
| 3 | Compound (III)-(5) | 98 | 0.12 |
| 4 | Compound (III)-(9) | 97 | 0.12 |
| 5 | Compound (III)-(11) | 98 | 0.12 |
| 6 | Comparative Compound A | 84 | 0.07 |
| 7 | Comparative Compound B | 93 | 0.16 |

EXAMPLE 6

A cubic silver chloride of 0.34 μm in average grain size was chemically sensitized, followed by adding the following sensitizing dye in an amount of $5\times10^{-5}$ mol per 1 mol of silver halide and further adding a surface active agent and 2,4-dichloro-6-hydroxy-1,3,5-triazine (Na salt). This emulsion was coated on a polyester film support at a coverage of 5 g/m² in terms of silver.

Sensitizing dye

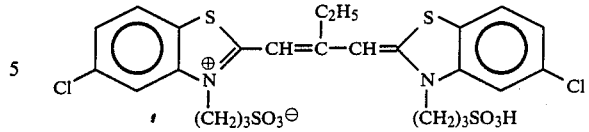

The sample was exposed through an optical wedge for $10^{-5}$ second and developed with PQ developer at 30° C. for 60 seconds and was subjected to sensitometry. Amount of antifoggant added to the emulsion was $2\times10^{-3}$ mol per 1 mol of silver halide. The following results were obtained.

| Sample | Antifoggant | Relative density | Fog |
|---|---|---|---|
| 1 (control) | No | 100 | 0.09 |
| 2 | Compound (III)-(1) | 103 | 0.03 |
| 3 | Compound (III)-(7) | 103 | 0.03 |
| 4 | Comparative Compound B | 94 | 0.07 |
| 5 | Comparative Compound D | 90 | 0.07 |

1 Comparative Compound D

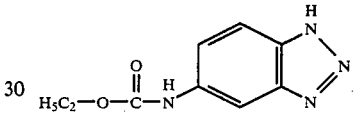

EXAMPLE 7

Normally used surface active agent and hardener were added to an emulsion for chlorobromide photographic paper which comprised silver halide of 1 mol % of silver iodide, 47 mol % of silver bromide and 52 mol % of silver chloride and this emulsion was divided into six parts.

One of them was used as a control sample and to each of other parts was added $4\times10^{-3}$ mol (per 1 mol of silver halide) of the compound of the present invention or the following comparative compound dissolved in methanol. All of these emulsions were coated on a polyethylene-coated paper support at a coverage of 1.5 g/m² in terms of silver.

These samples were exposed through an optical wedge and developed with D-72 developer at 20° C. for 90 seconds. These samples were subjected to sensitometry. Separately, samples which had not been exposed were developed with D-72 developer at 30° C. for 5 minutes and fog density was measured to obtain the following results.

The following two compounds were used as comparative compounds.

Comparative Compound A

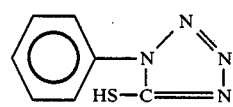

Comparative Compound B

-continued

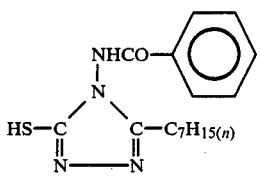

| Samples | Antifoggant | Relative density | Fog |
|---|---|---|---|
| 1 (control) | No | 100 | 0.22 |
| 2 | Comparative Compound A | 82 | 0.05 |
| 3 | Comparative Compound B | 85 | 0.07 |
| 4 | Compound (IV)-(1) | 95 | 0.05 |
| 5 | Compound (IV)-(4) | 90 | 0.06 |
| 6 | Compound (IV)-(19) | 93 | 0.05 |

EXAMPLE 8

Sample 1 of Example 7 (photographic paper containing no antifoggant) was developed with D-72 developer containing $2 \times 10^{-3}$ mol/l of antifoggant in the same manner as in Example 7 to obtain the following results.

| Developer | Antifoggant | Relative sensitivity | Fog |
|---|---|---|---|
| 1 (control) | No | 100 | 0.22 |
| 2 | Compound (IV)-(1) | 95 | 0.07 |
| 3 | Compound (IV)-(19) | 93 | 0.06 |
| 4 | Compound (IV)-(20) | 92 | 0.07 |
| 5 | Compound (IV)-(9) | 96 | 0.07 |
| 6 | Comparative Compound A | 84 | 0.07 |
| 7 | Comparative Compound B | 85 | 0.08 |

EXAMPLE 9

A cubic silver chloride of 0.34 μm in average grain size was chemically sensitized, followed by adding the following sensitizing dye in an amount of $5 \times 10^{-5}$ mol per 1 mol of silver halide and further adding a surface active agent and 2,4-dichloro-6-hydroxy-1,3,5-triazine (Na salt). This emulsion was coated on a polyester film support at a coverage of 5 g/m² in terms of silver.

Sensitizing dye

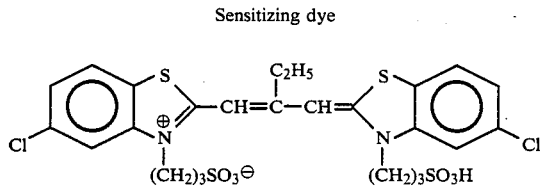

The sample was exposed through an optical wedge for $10^{-5}$ second and developed with PQ developer at 30° C. for 60 seconds and was subjected to sensitometry. Amount of antifoggant added to the emulsion was $2 \times 10^{-3}$ mol per 1 mol of silver halide. The following results were obtained.

| Sample | Antifoggant | Relative density | Fog |
|---|---|---|---|
| 1 (control) | No | 100 | 0.09 |
| 2 | Compound (VI)-(1) | 93 | 0.03 |
| 3 | Compound (VI)-(9) | 92 | 0.04 |
| 4 | Comparative Compound A | 87 | 0.03 |

What is claimed is:

1. A method for photographic processing of a silver halide photographic light-sensitive material which comprises imagewise exposing a silver halide photographic light-sensitive material and then developing the exposed light-sensitive material in the presence of at least one compound selected from the group consisting of the compounds represented by the following formulas (I)—(IV):

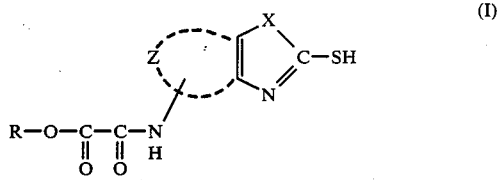

(I)

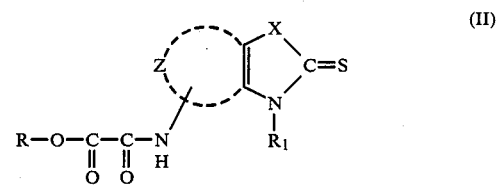

(II)

wherein Z represents a group of atoms necessary to form a condensed aromatic ring which may have a substituent in addition to

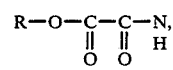

R represents a hydrogen atom or a monovalent organic group, $R_1$ represents a hydrogen atom or a substituted or unsubstituted alkyl group and X represents an oxygen atom, a sulfur atom, selenium atom or $>N-R_2$ wherein $R_2$ represents a hydrogen atom or a substituted or unsubstituted alkyl group;

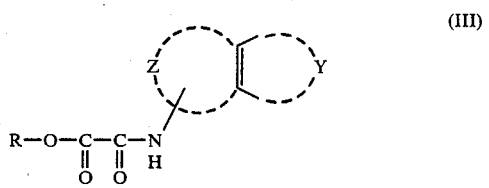

(III)

wherein Y represents a group of atoms necessary to form a heterocyclic ring having two or more nitrogen atoms, Z represents a group of atoms necessary to form a condensed aromatic ring which may have a substituent in addition to

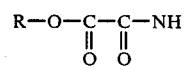

and R represents a hydrogen atom or a monovalent organic group; and

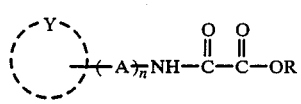 (IV)

wherein Y represents a group of atoms necessary to form a nitrogen-containing heterocyclic ring containing no condensed aromatic ring, R represents a hydrogen atom or a monovalent organic group, A represents an arylene group and n is 0 or 1.

2. A method according to claim 1 wherein the compound is present in a developer used for the development.

3. A method according to claim 1 wherein the compound is present in the silver halide photographic light-sensitive material.

4. A method according to claim 2 wherein the amount of the compound is $10^{-5}$–$10^{-1}$ mol/l.

5. A method according to claim 3 wherein the amount of the compound is $10^{-6}$–$10^{-2}$ mol per 1 mol of silver halide.

6. A silver halide photographic light-sensitive material which comprises a support and, provided thereon, at least one photographic layer including silver halide emulsion layer, said photographic layer containing at least one compound selected from the group consisting of the compounds represented by the following formulas (I)–(IV):

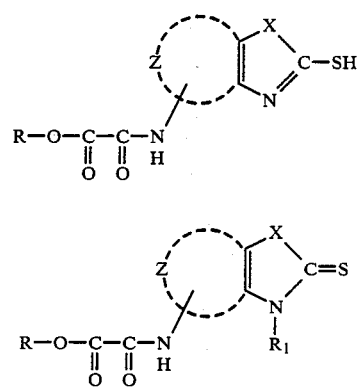

(I)

(II)

wherein Z represents a group of atoms necessary to form a condensed aromatic ring which may have a substituent in addition to

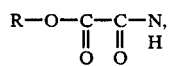

R represents a hydrogen atom or a monovalent organic group, $R_1$ represents a hydrogen atom or a substituted or unsubstituted alkyl group and X represents an oxygen atom, a sulfur atom, a selenium atom or N—$R_2$ wherein $R_2$ represents a hydrogen atom or a substituted or unsubstituted alkyl group;

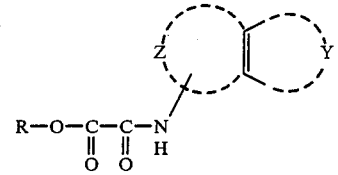 (III)

wherein Y represents a group of atoms necessary to form a heterocyclic ring having two or more nitrogen atoms, Z represents a group of atoms necessary to form a condensed aromatic ring which may have a substituent in addition to

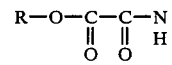

and R represents a hydrogen atom or a monovalent organic group; and

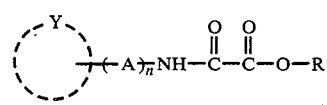 (IV)

wherein Y represents a group of atoms necessary to form a nitrogen-containing heterocyclic ring containing no condensed aromatic ring, R represents a hydrogen atom or a monovalent organic group, A represents an arylene group and n is 0 or 1.

7. A silver halide photographic light-sensitive material according to claim 6 wherein the amount of the compound is $10^{-6}$–$10^{-2}$ mol per 1 mol of silver halide.

8. A developer used for photographic processing of photographic light-sensitive material which contains at least one compound selected from the group consisting of the compounds represented by the following formulas (I)–(IV):

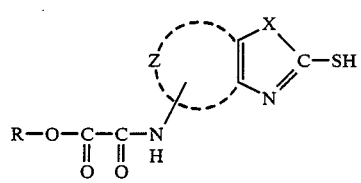

(I)

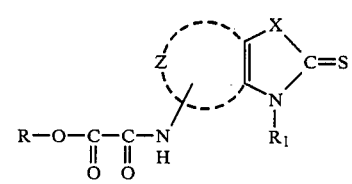

(II)

wherein Z represents a group of atoms necessary to form a condensed aromatic ring which may have a substituent in addition to

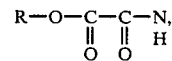

R represents a hydrogen atom atom or a monovalent organic group, $R_1$ represents a hydrogen atom or a substituted or unsubstituted alkyl group and X represents an oxygen atom, a sulfur atom, a selenium atom or >N—$R_2$ wherein $R_2$ represents a hydrogen atom or a substituted or unsubstituted alkyl group;

(III)

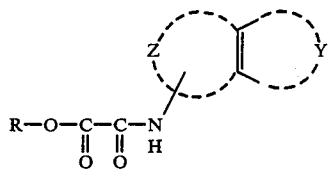

wherein Y represents a group of atoms necessary to form a heterocyclic ring having two or more nitrogen atoms, Z represents a group of atoms necessary to form a condensed aromatic ring which may have a substituent in addition to

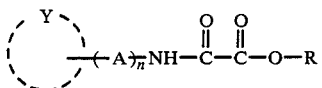

and R represents a hydrogen atom or a monovalent organic group; and (IV)

wherein Y represents a group of atoms necessary to form a nitrogen-containing heterocyclic ring containing no condensed aromatic ring, R represents a hydrogen atom or a monovalent organic group, A represents an arylene group and n is 0 or 1.

9. A developer according to claim 8 wherein amount of the compound is $10^{-5}$–$10^{-1}$ mol/l.

* * * * *